United States Patent [19]

Portner et al.

[11] Patent Number: 4,756,302

[45] Date of Patent: Jul. 12, 1988

[54] BLOOD PUMPING SYSTEM AND METHOD

[75] Inventors: Peer M. Portner, Kensington; Jal S. Jassawalla, San Francisco; Phillip J. Miller, Berkeley, all of Calif.

[73] Assignee: Novacor Medical Corporation, Oakland, Calif.

[21] Appl. No.: 933,490

[22] Filed: Nov. 20, 1986

[51] Int. Cl.$^4$ .............................................. A61B 19/00
[52] U.S. Cl. ........................................ 128/1 D; 623/3
[58] Field of Search ............... 128/1 D, 708; 417/412, 417/413; 623/3

[56] References Cited

U.S. PATENT DOCUMENTS

| | | | |
|---|---|---|---|
| 3,911,898 | 10/1975 | Leachman | 128/1 D |
| 3,966,358 | 1/1976 | Heimes et al. | 128/1 D |
| 4,046,137 | 9/1977 | Curless et al. | 128/1 D |
| 4,143,661 | 3/1979 | LaForge et al. | 128/419 R |
| 4,152,786 | 5/1979 | Clark et al. | 3/1.7 |
| 4,167,046 | 9/1979 | Portner et al. | 3/1.7 |
| 4,175,264 | 11/1979 | Schiff | 128/1 D |
| 4,384,829 | 5/1979 | Conley et al. | 417/412 |
| 4,457,673 | 7/1984 | Conley et al. | 417/412 |
| 4,565,497 | 1/1986 | Miller et al. | 623/3 |
| 4,611,578 | 9/1986 | Heimes | 128/1 D |
| 4,662,358 | 5/1987 | Farrar et al. | 128/1 D |
| 4,666,443 | 5/1987 | Portner | 128/1 D |

Primary Examiner—Max Hindenburg
Attorney, Agent, or Firm—Fitch, Even, Tabin & Flannery

[57] ABSTRACT

A heart-assist system and a method for operating same are described in which a pump is connected to a ventricle to receive output therefrom. An actuator operates to cause the pump to conduct a fill cycle in which it receives output from the ventricle to which it is connected, and to conduct an eject cycle in which the contents of the pump are expelled. The time of initiation of at least one of the fill cycle and the eject cycle is varied in relation to systole of the ventricle to which the pump is connected to thereby vary the loading of the ventricle. Several techniques for detecting termination of systole are described including a compliant stop on the pump.

18 Claims, 5 Drawing Sheets

BLOOD PUMPING SYSTEM AND METHOD

This invention relates generally to blood pumping systems and methods and, more particularly, to an improved heart-assist system and method employing a pump connected with a ventricle to receive output therefrom.

Various types of prosthetic devices for providing or assisting cardiac output and which may be implanted in patients are well-known. One type of such a device is shown and described in U.S. Pat. No. 4,457,673, issued July 3, 1984, and assigned to the assignee of the present invention. The pump described in the foregoing patent is designed principally for use as a ventricular assist device (initially intended for the left ventricle) to be implanted in a patient, typically in the abdominal cavity. The device is connected such that, upon contraction or systole of the left ventricle, it receives blood therefrom and thereby partially or completely fills. Upon cessation of systole, the pump contracts to expel its contents into the circulatory system of the patient. As such, the pump at least partially takes over the work (load) of the ventricle from which it receives blood, thereby relieving the ventricle of loading.

The device described in the aforesaid patent is useful as a permanently implanted device in cases where the function of the left ventricle of the patient is permanently impaired, or as a temporary measure in cases where the left ventricle of the patient is capable of recovery if unloaded for a particular period of time or as a temporary bridge to transplant while awaiting a donor heart. The device may be operated from implanted power supply as described in U.S. Pat. No. 4,143,661, or may be operated via transcutaneous leads from an outside console.

It is generally believed by surgeons, other physicians, and professionals associated with the use of heart-assist devices that, in some cases, the substantial unloading of the left ventricle on a permanent basis, or the sudden loading of the left ventricle upon termination of temporary use of an assist device, are undesirable. The terms "loading" and "unloading" as used herein refer to the relative level of left ventricular pressure, as a consequence of the functioning of the assist device to which the ventricle is connected, as compared with left ventricular pressure when connected only to the circulatory system. First of all, in the case of a permanently implanted assist device, permanent substantial unloading of the left ventricle being assisted can result in atrophy of the heart muscle. Such an occurrence would remove a safety factor from the patient inasmuch as the patient's own heart would be unable to even temporarily respond to the patient's circulatory needs in the event of a failure of the implanted device. In the case of temporary implantation, sudden reloading of the heart muscle after utilization of the assist device for a period of time could result in an undue strain on the suddenly reloaded heart. Other undesirable effects in the above described situations have been postulated by those skilled in the art.

Accordingly, it is an object of the present invention to provide an improved ventricular assist system.

More particularly, an object of the present invention is to provide a ventricular assist system and a method for operating same in which a predetermined loading of the assisted ventricle may be selected.

Another object of the invention is to provide a ventricular assist system and method for operating same in which the phase of the assist pump may be varied in relation to the systole of the ventricle being assisted so as to preselect a desired loading on such ventricle.

Other objects of the invention will become apparent to those skilled in the art from the following description, taken in connection with the accompanying drawings wherein:

Very generally, the heart-assist system of the invention operates such that a pump connected to a left ventricle receives output therefrom. The pump includes an actuator which operates to cause the pump to conduct a fill cycle in which it receives output from the ventricle to which it is connected, and to conduct an eject cycle in which the contents of the pump are expelled into the patient's circulation. A control is connected to the actuator for varying the time of initiation of at least one of the fill cycle and eject cycle in relation to systole of the ventricle to which the pump is connected to thereby vary the loading of such ventricle.

Figure 1:
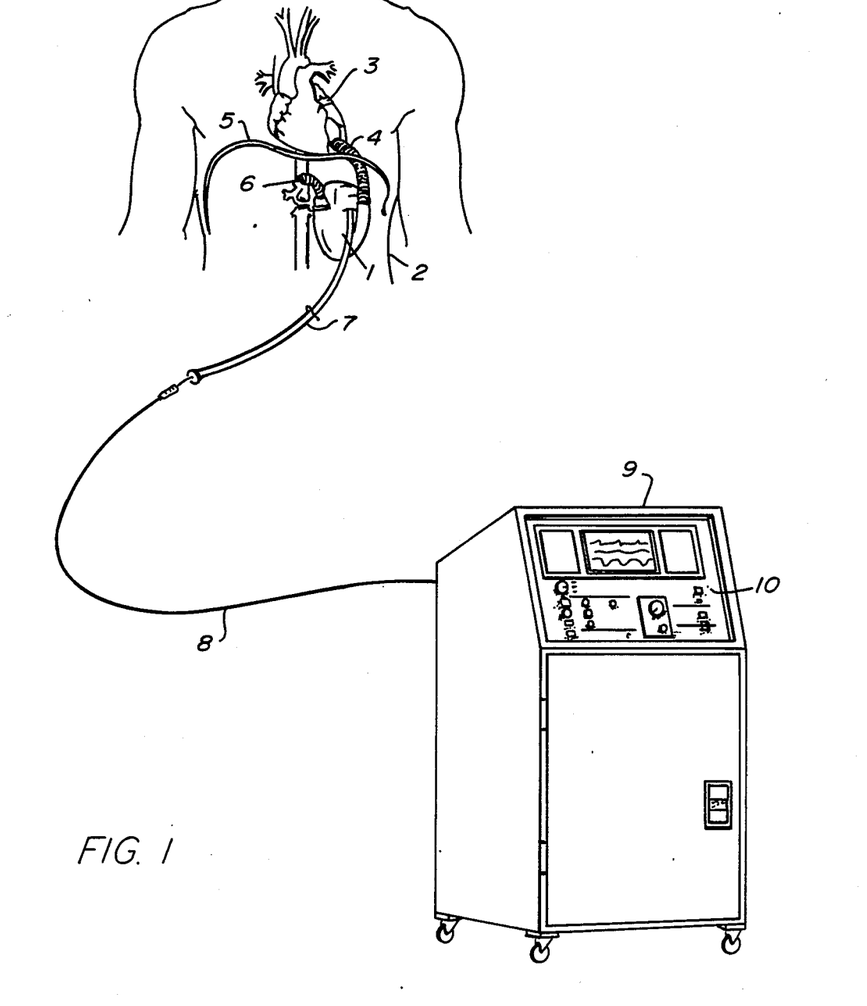
FIG. 1 is a schematic diagram of a ventricular assist system constructed in accordance with the invention.

Referring now more particularly to FIG. 1, the blood pump 1 of the system of the invention is shown implanted within the body of a patient 2. The specific details of the blood pump 1 will be described below. The blood pump is connected to the left ventricle 3 of the patient via an inflow conduit 4 of a suitable material, such as woven dacron (a trademark), which pierces the pericardial portion of the patient's diaphragm 5. Actual connection of the inflow conduit 4 to the left ventricle 3 may be via a suitable cannula (not shown) inserted, via the apex, into the left ventricular cavity. An outflow conduit 6 of a suitable material, such as woven dacron (a trademark), connects the outflow of the pump 1 to the supraceliac aorta or other suitable systemic artery by an anastomosed graft.

In the illustrated application, the implanted pump is shown powered from an external console via percutaneous leads. However, it is fully within the scope of the invention to utilize other types of power sources including partially or fully implanted systems. An example is described in the aforementioned U.S. Pat. No. 4,143,661. Control and power leads for the implanted pump 1 pass through a suitable biocompatible percutaneous vent sheath cable 7. The cable 7 is connected via a suitable extension cable 8 to a control console 9. The control console 9 powers and controls the implanted pump 1 and provides for monitoring critical system and patient parameters. The console 9 includes a control panel 10 provided with a variety of suitable switches and knobs for setting system control modes and making parameter adjustments, as more fully described below. The control panel also provides for the monitoring of patient and system parameters displayed via signals obtained from patient transducers, such as ECG, aortic and left ventricular pressures. These parameters may be obtained by means known to those skilled in the art. Additionally, the pump volume may be determined via sensors located in the pump as described below. Suitable alarm capabilities may also be utilized in the console to detect out-of-limit patient variables or malfunction in the pumping system. Appropriate redundancy may also be provided for reliability standards.

In operation, the blood pump 1 which is connected with the left ventricle 3 fills during left ventricular systole by offering low resistance to the outflow from the left ventricle through the inflow conduit 4. Synchronized with systole, at, before, or after termination thereof, as explained below, the pump 1 begins an eject cycle in which it contracts, as will be explained below, to expel its contents through the outflow conduit 6 into the patient's circulatory system (via the supraceliac aorta in the arrangement illustrated). The eject cycle is initiated by energization of a solenoid in the pump actuator. Such energization signals are provided from a suitable power supply in the console 9 (or from an implanted unit if desired).

The system of the invention and the method of the invention may be employed, by way of example, in connection with a blood pump of the general type such as that described in U.S. Pat. Nos. 4,167,046 and 4,457,673, assigned to the assignee of the present invention. This type of pump includes a pair of opposed pusher plates which act on opposite sides of a disc-shaped seamless sac to expel fluid therefrom. Opposed beam springs are each pivotally connected at one end to the associated pusher plates and are attached at the other spring end on an armature assembly pivotally connected to a frame. Each assembly includes a preload stop which holds the associated spring in a relatively less stressed position. Coordinated movement of the two assemblies toward one another, by solenoid actuation, moves the two springs towards their relatively more stressed positions. Stress relief in the beam springs acts to move the two pusher plates symmetrically toward one another.

Figure 2:
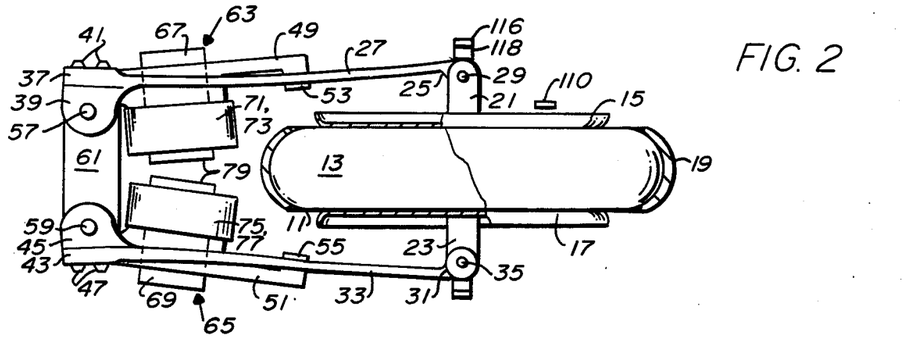
FIGS. 2, 3 and 4 are cross-sectional schematic views of a pump which may be used in the system of the invention, illustrating different pumping conditions.
Figure 3:
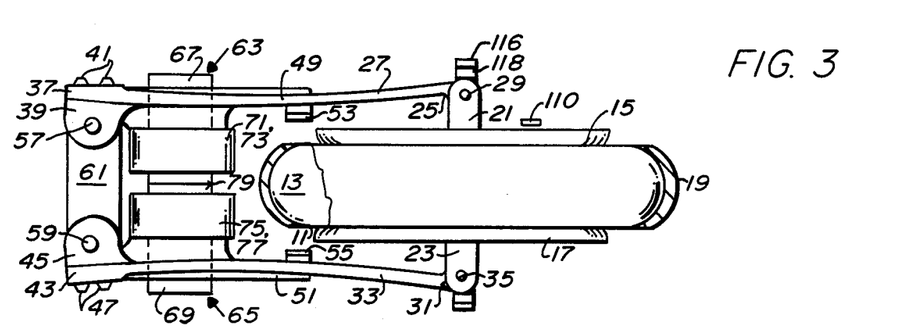
Figure 4:
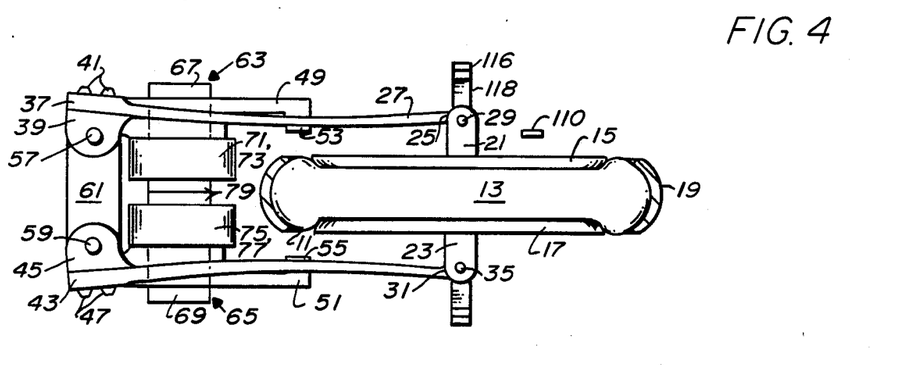

More specifically, the pump 1 which is for the purpose of serving as a left ventricular device implanted in a human patient, includes an enclosure 11 defining a pumping chamber 13 (see FIGS. 2 through 4.) Opposed pusher plates 15, 17 are disposed on opposite sides of the enclosure 11 and are in contact therewith. Movement of the plates toward one another acts to compress the flexible enclosure and force the contents of the chamber out through a suitable outlet duct, not shown. Greater detail of this pump chamber configuration is given in the aforementioned U.S. patents. An annular support 19 surrounds the flexible enclosure 11 to position it with respect to the remaining portions of the pump, including the actuator mechanism.

In the illustrated pump, two pairs of opposed beam springs 27, 33 are used, although only one spring in each pair is visible in FIGS. 2-4. However, one pair of opposed beam springs will suffice in some applications, and an actuator of the latter design is shown and described in U.S. Pat. No. 4,565,497 issued Jan. 21, 1986. Opposed pairs of posts 21 and 23, extend from plates 15, 17 respectively, at the positions seen in FIG. 4. Posts 21 are pivotally connected to the enlarged ends 25 of a pair of beam springs 27 by pins 29. Similarly, posts 23 are pivotally connected to the enlarged ends 31 of a pair of beam springs 33 by pivot pins 35.

The ends of beam springs 27 opposite ends 25 are provided with portions 37 of slightly enlarged cross-section. The sections 37 are bolted to a support 39 by bolts 41 passing through the portions 37 into the support 39. Similarly, the ends of the beams 33 opposite the ends 31 are provided with enlarged thickness portions 43 which are bolted to a support 45 by means of bolts 47.

Each of the supports 39 and 45, respectively, is provided with a pair of arms 49 and 51, respectively, extending therefrom coextensively with the corresponding beam springs 27 and 33. Projections or preload stops 53 are provided on the free ends of the arms 49 projecting under the corresponding one of the beam springs 27. Similar preload stops 55 are provided on the free ends of the arms 51 projecting over the corresponding one of the beam springs 33. For reasons which will be explained subsequently, the mating surfaces of the portions 37 of the beam springs 27 and the support 39 lie in a plane such that the engaging points of the preload stops 53 project beyond that plane and, accordingly, preload the beam springs 27 in bending stress. A similar relationship with the preload stops 55 and the mating surfaces of the support 45 and the portions 43 of the beam springs 33 provides a preload for the beam springs 33. The result is that each of the beam springs 27 and 33 is always stressed in bending by a minimum amount provided by the preload of the preload stops 53 and 55.

Each of the supports 39 and 45 is mounted for pivotal movement about an axis through a pivot pin 57 and 59, respectively. Thus, as the support 39 pivots on the pin 57, so likewise do the sections 37 of the beam springs 27 move pivotally about the axis. Similarly, as the support 45 pivots on the axis of the pin 59, so likewise the ends 43 of the beam springs 33 pivot about the axis of the pin 59 with the support 45. Each of the pins 57 and 59 is supported in a frame 61 which comprises a portion of the general frame (not shown) of the pump which includes the enclosure support.

For the purpose of pivoting the beam springs about the axes of the pins 57 and 59, solenoid means are provided. The solenoid means include a pair of solenoid armatures 63 and 65 mounted, respectively, on supports 39, 45. The supports 39, 45 and attached armatures 63, 65, respectively, each forms what is referred to herein as an armature assembly. Solenoid armature 63 includes a C-shaped core 67, the free ends of which extend through mating openings in the support 39. Similarly, the solenoid armature 65 includes a C-shaped core 69, the free ends of which extend through mating openings in the support 45. The open side of the core 67 faces the open side of the core 69 and the free ends 79 are aligned. Each leg of the C-shaped core 67 is wound by a coil 71 and 73. Similarly, each leg of the C-shaped core 69 is wound by a coil 75 and 77, respectively. Energization of the coils 71, 73, 75, and 77, by suitable control means, not shown, causes the ends of the solenoid cores to be attracted toward each other.

The operation of the actuator mechanism and pump may be observed sequentially in FIGS. 2-4. FIG. 2 illustrates the apparatus in a condition in which the pump chamber 13 is full and the solenoid armatures 63 and 65 are unenergized. In this condition, the arms 49 and 51 are swung open to their widest conditions as are the beam springs 27 and 33. In this condition, a preload bias is provided to the springs by the preload stops 53 and 55.

The ejection stroke is begun when the power circuits 87 (FIG. 5) energize the solenoid coils 71, 73, 75, and 77.

When energized, the armatures 63 and 65 are drawn toward each other, moving the arms 49 and 51 to the position shown in FIG. 3. In this position, the inertia of the filled pump chamber 13 and compressible sac 11 retain the ends 25 and 31 of the beam springs 27 and 23 essentially in the same position as in FIG. 2. The preload stops 53 and 55 are moved away from the springs, with pivoting of supports 39, 45, causing the springs to be stressed to a more loaded condition in which they contain greater stored energy.

After closure to the position of FIG. 3, the solenoid means are held there by a relatively small latching current. If additional holding force is needed, a small permanent magnet may be used. The force of the latter may be overcome when necessary by a small reverse current in the solenoid coils.

From the condition of FIG. 3, the natural tendency for the beam springs 27 and 33 to relieve the stressed condition results in the plates 15 and 17 being moved toward each other, thus expelling the contents in the pump chamber 13. At the end of the pump stroke, shown in FIG. 4, the beam springs have returned to their less stressed condition abutting the preload stops 53 and 55. Once this has occurred, the solenoid coils are de-energized or unlatched.

The apparatus is returned to the condition shown in FIG. 2 as the result of the cardiac systole. The solenoid gap thus increases as the supports 39 and 45 pivot about the pivot pins 57 and 59, respectively, as the plates 15 and 17 push out the ends 25 and 31 of the springs 27 and 33. With the pump connected to the left ventricle, as in FIG. 1, and with the solenoid means not energized, the pump offers little resistance to discharge of the ventricle (i.e., essentially no loading).

Figure 5:
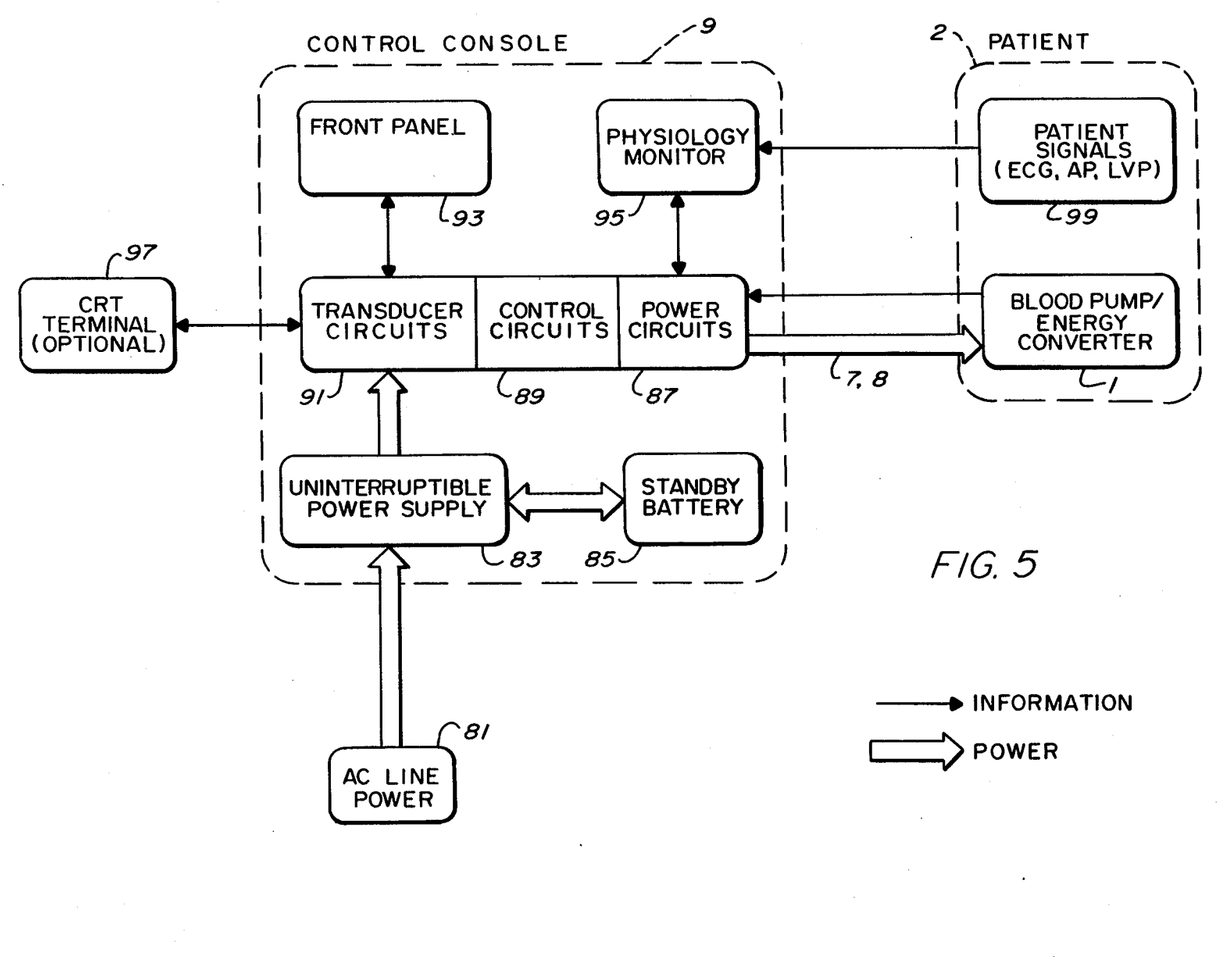
FIG. 5 is a block diagram of a ventricular assist system constructed in accordance with the invention.

As described above, initiation of the eject cycle of the pump 1 is accomplished by energization of the solenoid armatures 63 and 65. Such energization, as previously explained, emanates from the control console 9 or other suitable implanted device. In FIG. 5, a block diagram illustrating the relationship of the control console to the other elements of the system is shown. The control console 9 is powered from a suitable AC power line 81 which supplies power to an uninterruptable power supply 83 of suitable conventional design. A standby battery 85 is provided in the console 9 which is charged via the power supply 83 and which provides power through the power supply 83 in the event of failure of power from the AC power line 81. The power supply 83 also provides power to the energy converter or solenoid means of the pump 1 via the cable connections 7, 8 through suitable power circuits 87 contained within the console 9.

In FIG. 5, the power circuits are shown in the same overall box or block as the control circuits 89 and the transducer circuits 91 to indicate the commonality of many portions of such circuits and their interconnection with the power supply 83 and with front panel components and physiology monitor indicated in the blocks 93 and 95. The power circuits, control circuits and transducer circuits 87, 89 and 91 may also be connected, if desired, to a cathode ray tube display terminal 97 which may or may not be located on the front panel 10 of the control console 9. Patient signals, such as ECG, aortic pressure, and left ventricle pressure, may be provided by appropriate and known transducers, indicated by the block 99, within the patient 2.

Figure 6:
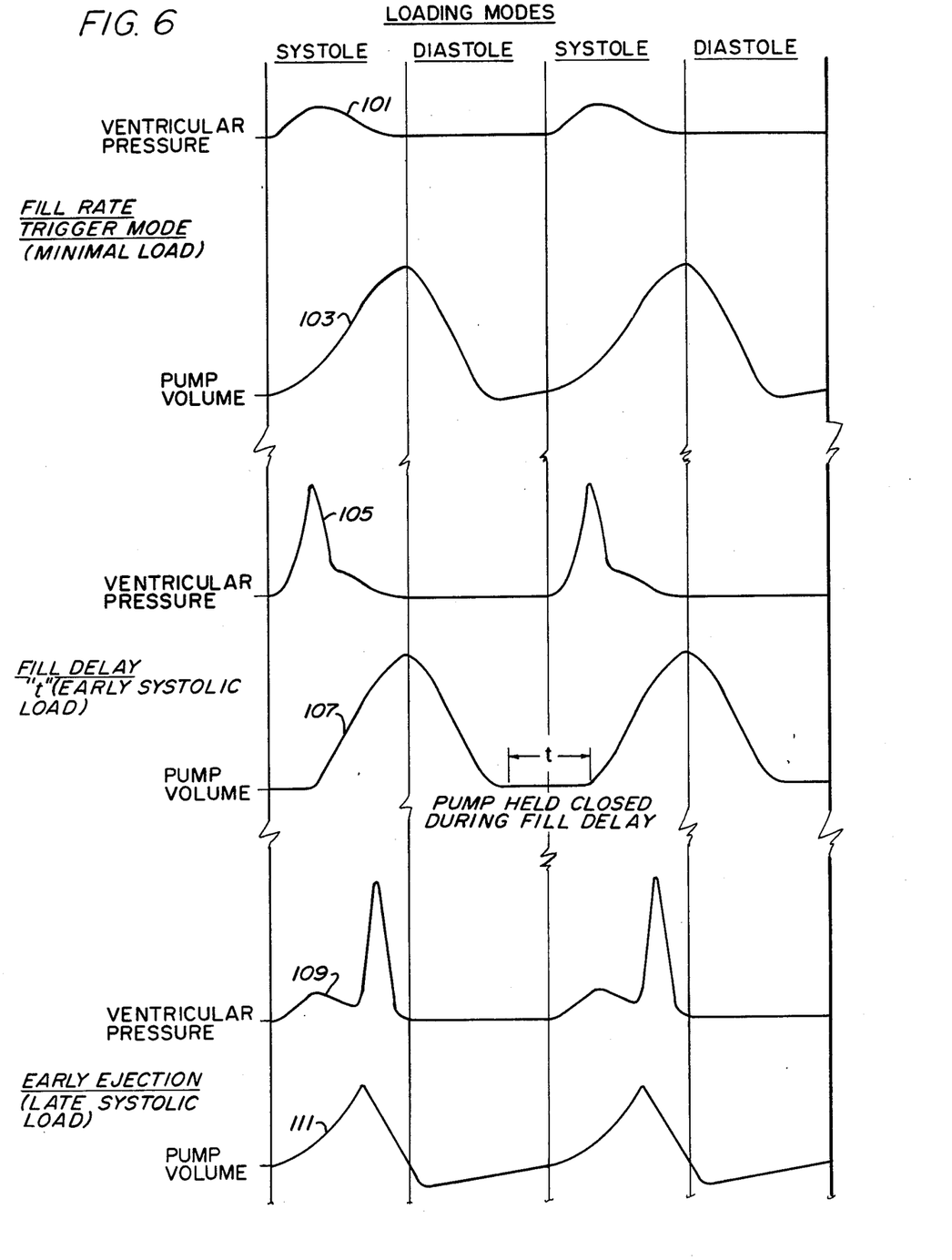
FIG. 6 is a series of plots illustrating the relationship of ventricular pressure to pump volume in various loading modes in the system of the invention.

Referring now to FIG. 6, representations of three different loading modes for the left ventricle by the assist system of the invention is made. The upper pair of curves compares the ventricular pressure with the pump volume in an operating mode, known as the fill rate trigger mode, wherein essentially minimal loading of the ventricle occurs. The upper curve, 101, represents ventricular pressure which may be seen to rise and fall during systole and remain at very low levels during diastole. In this operation mode, the pump volume, represented by the curve 103, increases from minimum to maximum during systole as the fill cycle is set to coincide with systole. Upon conclusion of systole, sensed as will be described below, an ejection cycle is initiated, expelling the contents of the pump during diastole of the ventricle to which the pump is attached.

A second mode of loading is illustrated by the middle pair of curves, with the curve 105 indicating the ventricular pressure and the curve 107 indicating the pump volume. In this mode, known as the fill delay or early load mode, the fill cycle of the pump is delayed from the beginning of ventricular systole. This delay causes the ventricular pressure to increase during the isovolumic contraction phase (before the aortic valve opens) and consequently partially loads the ventricle. Once the solenoid is de-energized and the ventricle begins discharging into the pump, ventricular pressure is reduced. Solenoid de-energization will typically be set to occur prior to termination of the isovolumoic contraction phase. However, it is possible if desired to delay solenoid de-energization beyond conclusion of the isovolumic contraction, in which case the ventricular pressure would increase sufficiently to open the aortic valve, and the ventricle will eject blood into the systemic circulation.

By varying the point of initiation of the fill cycle of the pump, namely, by displacing the curve 107 to the left or the right relative to systole, the duration of the higher pressure in the ventricle (i.e., the width of the higher portion of the curve 105 during systole) can be varied to precisely control the degree of loading of the ventricle during each heart cycle.

The lower pair of curves in FIG. 6 represent a third loading mode, namely the eject early, or late systole load mode. In this mode, the beginning of pump fill cycle is essentially coincident with the beginning of systole as was the case with the uppermost two curves, 101 in FIG. 6 and 113 in FIG. 7. However, in the eject early mode, the ventricular pressure, as represented by the curve 109, is increased by beginning the ejection mode of the pump before conclusion of systole. Thus, it may be seen that pump volume, represented by the curve 111, decreases during the ejection cycle prior to the end of ventricular systole, resulting in an increase of ventricular pressure at the end of systole as shown by the curve 109. By varying the position of the ejection cycle relative to termination of systole, the amount of loading, as represented by the higher portion of the curve 109 during systole may be regulated.

In order to determine the end of systole for the purpose of timing the initiation of the fill cycle and/or eject cycle, any suitable patient or pump system information may be employed. For example, pump ejection may be triggered by the QRS complex of the patient's ECG, detected by a suitable ECG detection system capable of detecting the QRS complex. Since the QRS occurs at the start of ventricular systole, the actual initiation of pump ejection is delayed from this event until the end of systole by manually (or automatically) setting a particular preselected interval on the control console. By adjusting such timing of the energization of the solenoid operated pump, the pump phasing can be set to achieve a desired ventricular loading or unloading.

Preferably, ventricular systole is sensed by utilizing a position sensor, shown schematically in FIGS. 2–4 at 110, suitably mounted within the pump, to detect the current volume of blood in the pump sac. Sensors for accomplishing this are known in the art and typically are conventional eddy-current type position transducers. Such devices operate to measure the spacing between a current signaling surface and a target surface according to changes produced by magnetic induction in the target surface. Such detectors are sold in combination with control circuitry and can be readily adapted to provide the desired information and fulfill size requirements.

By monitoring changes in the pump fill rate, which varies in response to ventricular contraction, one can determine the end of systole. Fill rate rises at the start of systole and falls near the end of systole as may be seen by the curves 103, 107 and 111 in FIG. 6. Pump ejection can be triggered at a desired interval from or coincident with the end of ventricular systole by detecting the drop in fill rate. The exact trigger point can be adjusted to occur at a predetermined interval from a preset fill rate threshold level. This threshold can be a particular percentage by which the fill rate must fall from the peak fill rate. By operating the system in this manner, dependence upon physiologic transducers whose lack of stability is well known is avoided, since all information comes from within the system itself.

Figure 7:
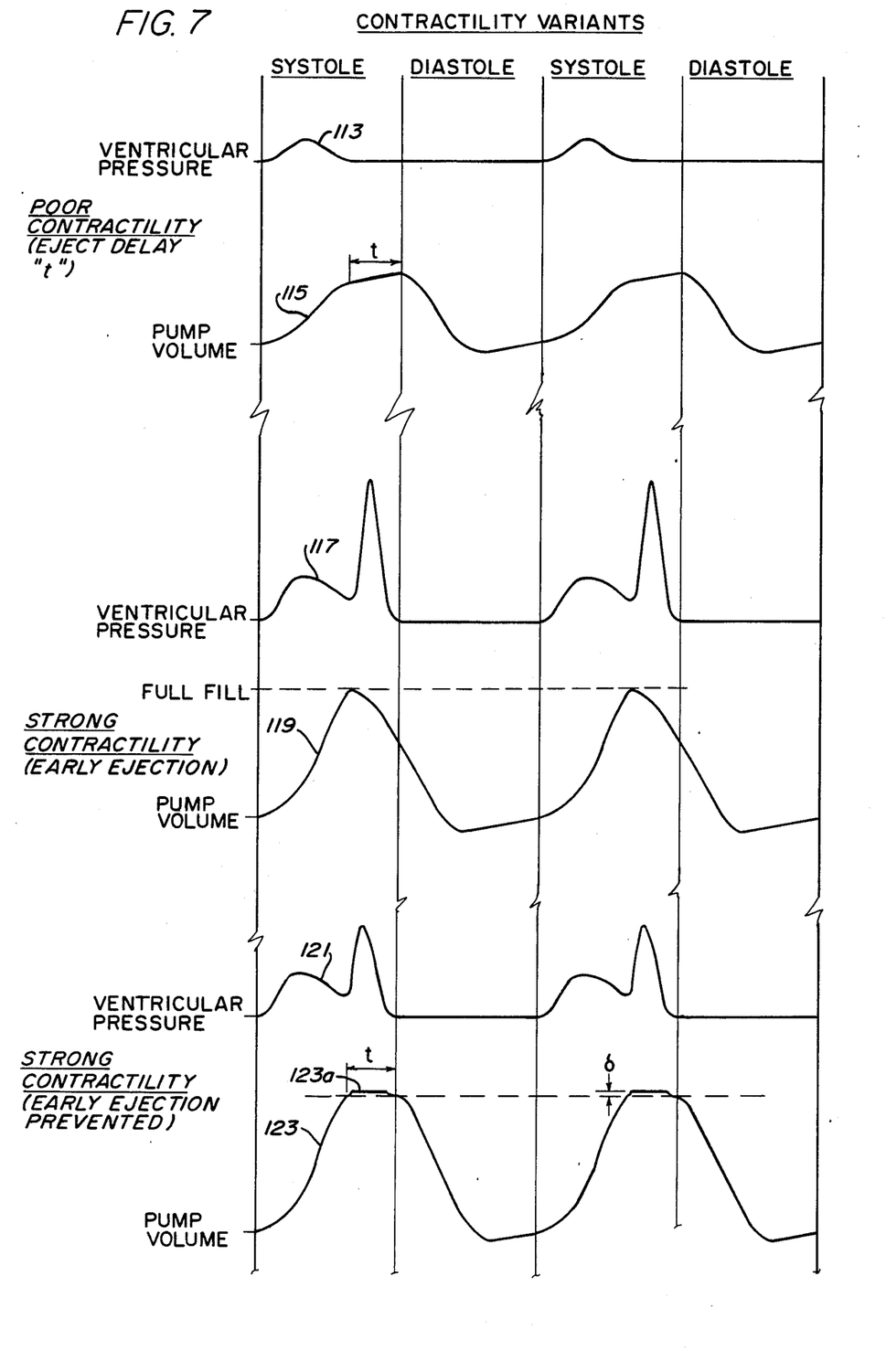
FIG. 7 is a series of plots illustrating the relationship of ventricular pressure to pump volume under various contractility variants which may be present in a patient.

Referring now to FIG. 7, the effect of variations in the contractility of the ventricle being assisted is illustrated. In the upper pair of curves, ventricular pressure is indicated by the curve 113 as contrasted with pump volume shown by the curve 115. In this situation, the curve 113 represents a ventricular pressure which is weak, such as might occur in a situation of a severely diseased heart. As may be seen, the ventricular pressure falls off toward the end of systole, resulting in a significant falloff in the rate of increase of pump volume during that period. In such a situation, the timing of the ejection stroke is delayed from the falloff in ventricular pressure and consequent falloff in fill rate an interval (designated "t" in FIG. 7) sufficient to insure that the ejection cycle will occur during ventricular diastole.

The pair of curves in the middle of FIG. 7 indicate ventricular pressure 117 and pump volume 119 during a situation wherein there is strong ventricular contractility. In this case, the pump volume reaches its maximum capacity (full fill position) early, with the pump fill rate declining to zero even though vertricular systole has not ended. The zero pump fill rate will falsely indicate the end of systole to the control system which is turn will initiate pump ejection prematurely. The co-pulsation of the pump and ventricle in such a case increases the load on the ventricle as shown in curve 117. In this sense, the situation is somewhat similar to that which occurs during the early eject or late load mode of operation illustrated by the lower two curves in FIG. 6.

In the event that ventricular loading of the type shown by the curve 117 is not desired, a lower level of loading may be achieved by placing a compliant stop in the pump as shown in FIGS. 2 through 5. The compliant stop, as illustrated schematically, comprises a curved or C-shaped bracket 116 which is positioned so that its ends extend to locations over the posts 21 and 23. Pads 118 of a compressible material, such as an elastomeric, engage the ends of the posts in the filled position. Although some additional loading of the left ventricle is shown by the curve 121, the loading is lessened. The compliant stop provides a slight mesa 123a on the curve 123 which last for a time t at an increased volume increment of δ. The mesa 123a can be used by the pump position transducers to sense the end of systole when the down step on the backside of the mesa 123a occurs. This occurs when the pressure within the ventricle no longer overcomes the compliance of the compliant stop. By detecting the end of systole as described, the beginning of pump ejection can be regulated to eliminate co-pulsation between the ventricle and the pump to minimize ventricular loading.

The system and method of the invention represent a significant improvement in ventricular assist systems and methods in which synchronization with the natural heart phases is readily achieved and in which a precise degree of loading/unloading of the heart may be selected. Such loading is useful to prevent atrophy of the heart muscle in the case of permanent circulatory support, or to help wean the patient from the assist device in the case of temporary use by enabling the heart to be gradually loaded in a controlled manner. These functions—unloading or loading—are controlled by the timing and phase of the fill cycle and eject cycle of the pump device. The degree of phase overlap may be controlled on either end of the ventricular systole to control the degree of ventricular loading.

Various modifications of the invention, in addition to those shown and described herein, will become apparent to those skilled in the art from the foregoing description and accompanying drawings. Such modifications are intended to fall within the scope of the appended claims.

What is claimed:

1. A heart-assist system comprising, pump means adapted for connection with a patient's ventricle to receive output therefrom, said pump means including actuator means operable to cause said pump means to conduct a fill cycle in which it receives output from the patient's ventricle to which it is connected, and to conduct an eject cycle in which the contents of said pump are expelled, and control means connected to said actuator, said control means including means for determining the systole of the patient's ventricle to which said pump means is connected, and means for varying the time of initiation of at least one of said fill cycle and said eject cycle in relation to systole of the ventricle to which said pump means is connected to thereby vary the loading of such ventricle.

2. A system according to claim 1 wherein said control means vary the time of initiation of said fill cycle.

3. A system according to claim 1 wherein said control means vary the time of initiation of said eject cycle.

4. A system according to claim 1 wherein said control means vary the time of initiation of both said fill cycle and said eject cycle.

5. A system according to claim 1 wherein said control means include sensor means for sensing the fill rate of said pump means.

6. A system according to claim 1 wherein said control means initiate said fill cycle a predetermined time interval from the attainment of a preselected fill rate of said pump means.

7. A system according to claim 1 wherein said control means include sensor means for sensing the QRS complex of the ECG of the ventricle.

8. A system according to claim 1 wherein said pump means include a compliant stop, and wherein said control means include sensor means connected to said compliant stop for sensing the termination of systole.

9. A system according to claim 1 wherein said control means determine the end of systole from a predetermined change in the fill rate.

10. A method for operating a heart-assist system which includes pump means adapted for connection in series with a patient's ventricle to receive output therefrom, the pump means including actuator means operable to cause the pump means to conduct a fill cycle in which it receives output from a patient's ventricle to which it is connected, and to conduct an eject cycle in which the contents of the pump means are expelled, said method comprising determining the systole of the patient's ventricle to which the pump means is connected, and varying the time of initiation of at least one of said fill cycle and said eject cycle in relation to systole of the patient's ventricle to which the pump means is connected to thereby vary the loading of such ventricle.

11. A method according to claim 10 wherein the time of initiation of the fill cycle is so controlled.

12. A method according to claim 10 wherein the time of initiation of said eject cycle is so controlled.

13. A method according to claim 10 wherein the time of initiation of both said fill cycle and said eject cycle are conrolled.

14. A method according to claim 10 wherein systole of the ventricle is determined by sensing the fill rate of the pump.

15. A method according to claim 14 wherein the end of systole is determined from a predetermined change in the fill rate.

16. A method according to claim 10 wherein systole of the ventricle is determined by sensing ventricular pressure.

17. A method according to claim 10 wherein systole of the ventricle is determined by sensing the QRS complex of the patient's ECG.

18. A method according to claim 10 wherein the fill rate of the pump means is sensed and a predetermined point is selected representing a falloff in said fill rate, and wherein the initiation of said fill cycle is set at a predetermined time from said preselected point.

* * * * *